US012018381B2

United States Patent
Rahimi et al.

(10) Patent No.: US 12,018,381 B2
(45) Date of Patent: Jun. 25, 2024

(54) LASER-INDUCED ATMOSPHERIC $Cu_xO$ FORMATION ON COPPER SURFACE WITH ENHANCED ELECTROCHEMICAL PERFORMANCE

(71) Applicant: Purdue Research Foundation, West Lafayette, IN (US)

(72) Inventors: Rahim Rahimi, West Lafayette, IN (US); Sotoudeh Sedaghat Hoor, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/892,014

(22) Filed: Aug. 19, 2022

(65) Prior Publication Data

US 2023/0072282 A1 Mar. 9, 2023

Related U.S. Application Data

(60) Provisional application No. 63/235,590, filed on Aug. 20, 2021.

(51) Int. Cl.
*C23C 26/00* (2006.01)
*A61B 5/145* (2006.01)

(52) U.S. Cl.
CPC .......... *C23C 26/00* (2013.01); *A61B 5/14532* (2013.01)

(58) Field of Classification Search
CPC ............................ C23C 26/00; A61B 5/14532
See application file for complete search history.

(56) References Cited

PUBLICATIONS

Zhuang, Z. et al. "An improved sensitivity non-enzymatic glucose sensor based on a CuO nanowire modified Cu electrode". Analyst, 133, pp. 126-132 (2008). (Year: 2008).*
Sedaghat, S et al. "Laser-Induced Mesoporous Nickel Oxide as a Highly Sensitive Nonenzymatic Glucose Sensor". ACS Appl. Nano Mater. 3, 6, 5260-5270 (Jun. 1, 2020). (Year: 2020).*

* cited by examiner

*Primary Examiner* — Alexander M Weddle
(74) *Attorney, Agent, or Firm* — Purdue Research Foundation

(57) ABSTRACT

A method of manufacturing a copper oxide ($Cu_xO$) structure onto a Copper (Cu) surface by fabricating an electroactive hierarchical $Cu_xO$ structure directly onto the Cu surface by laser-induced oxidation (LIO). The generated heat from the laser source provides energy for the oxidation of the Cu surface in the presence of atmospheric oxygen. The electroactive hierarchical $Cu_xO$ structure is a binder-free nano-textured structure. The electroactive hierarchical $Cu_xO$ structure may be used as a glucose sensor.

17 Claims, 13 Drawing Sheets

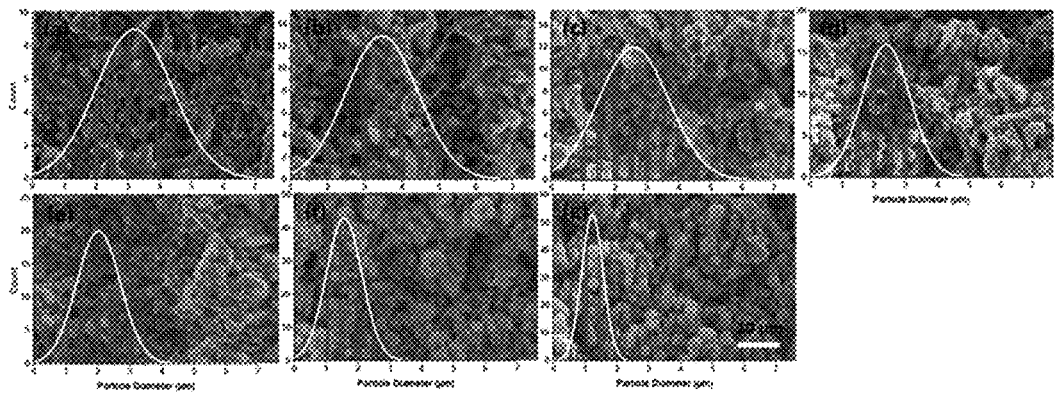
FIG. 3F
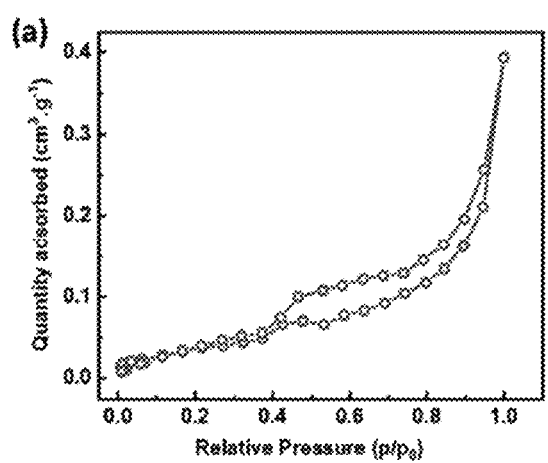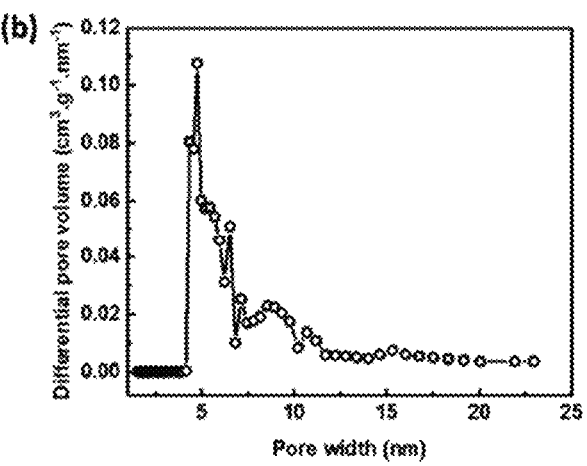
FIG. 4A          FIG. 4B

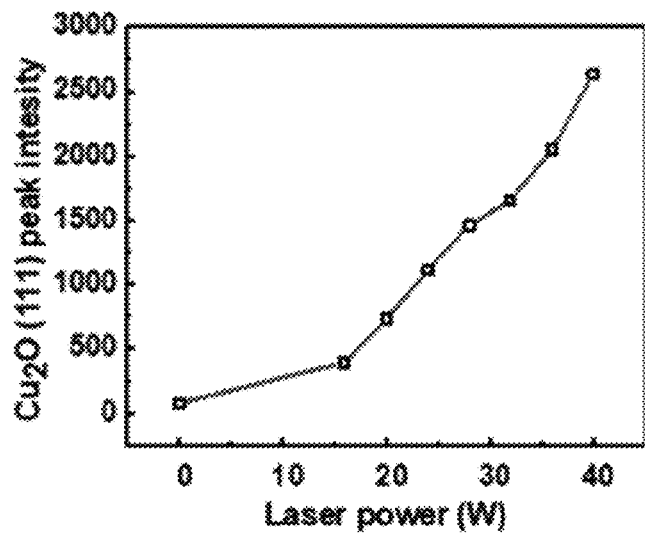
FIG. 6C
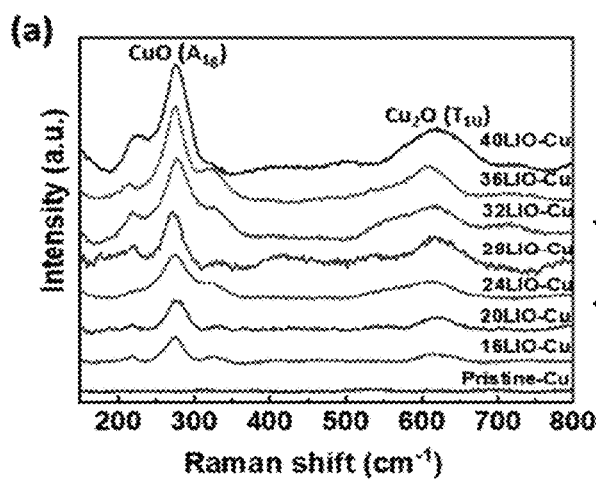 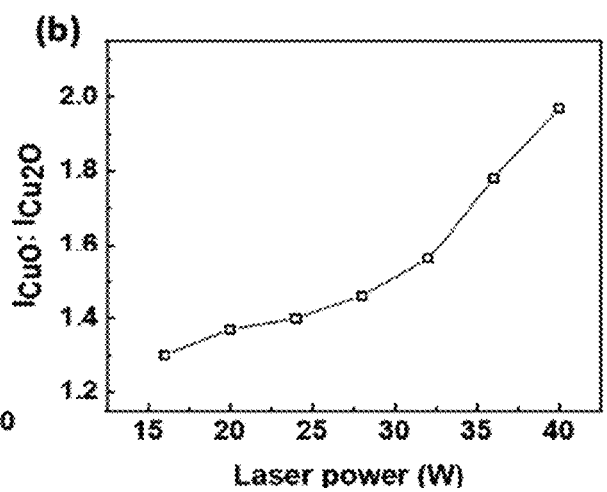
FIG. 7A  FIG. 7B

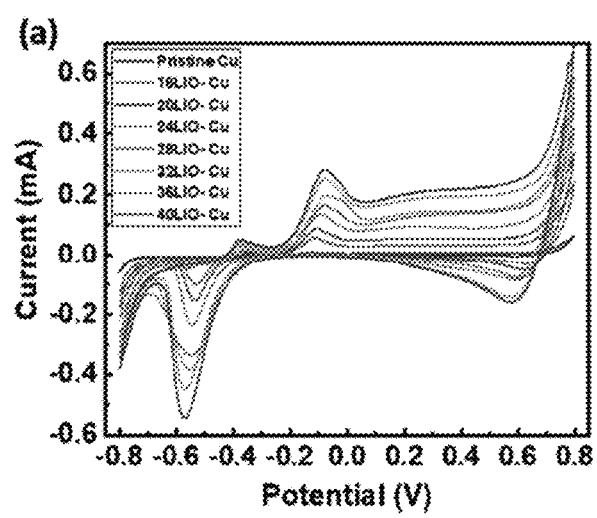
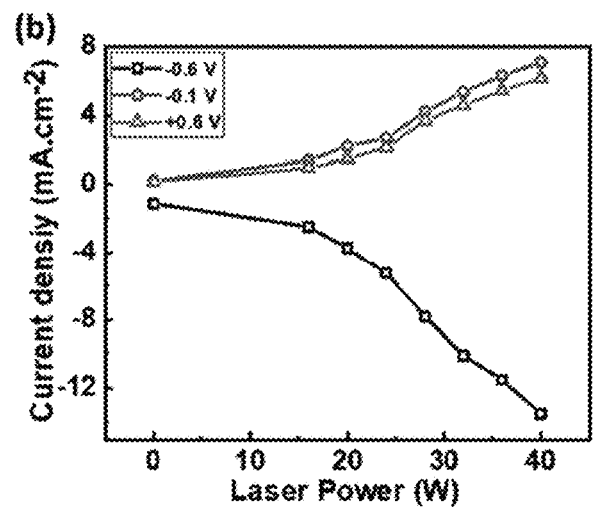
FIG. 8A  FIG. 8B

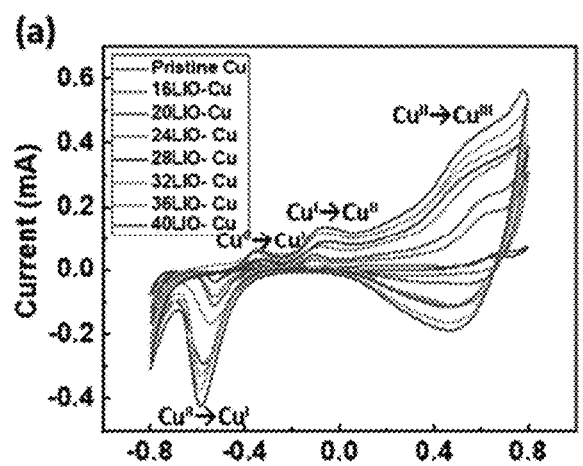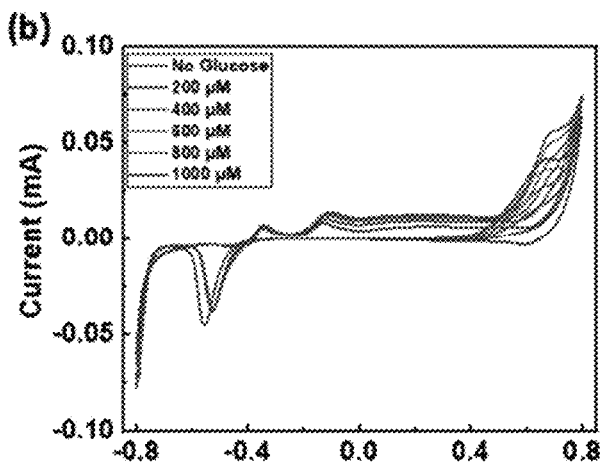
FIG. 9A  FIG. 9B
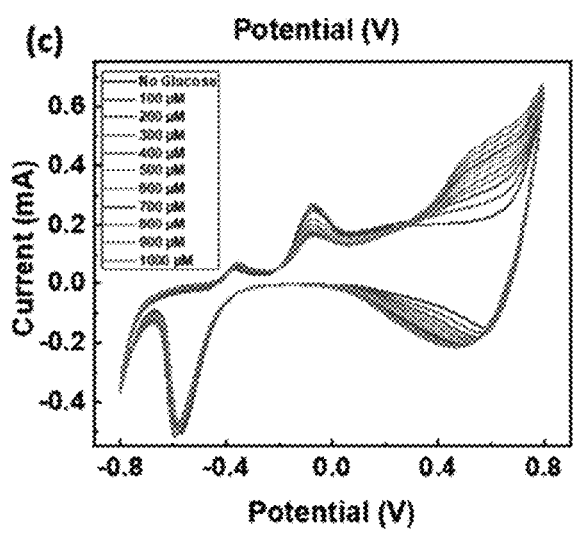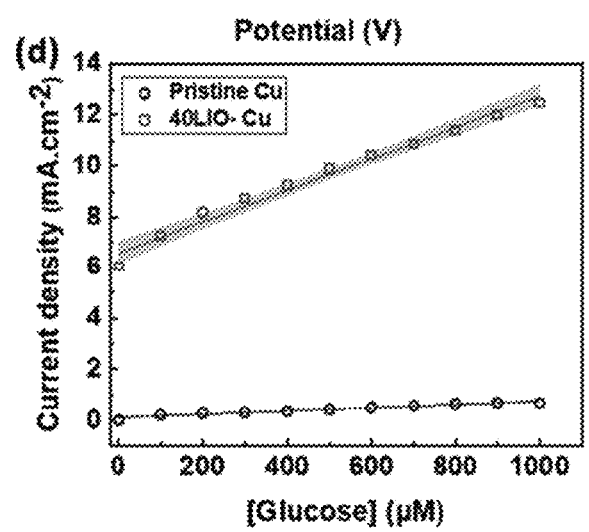
FIG. 9C  FIG. 9D

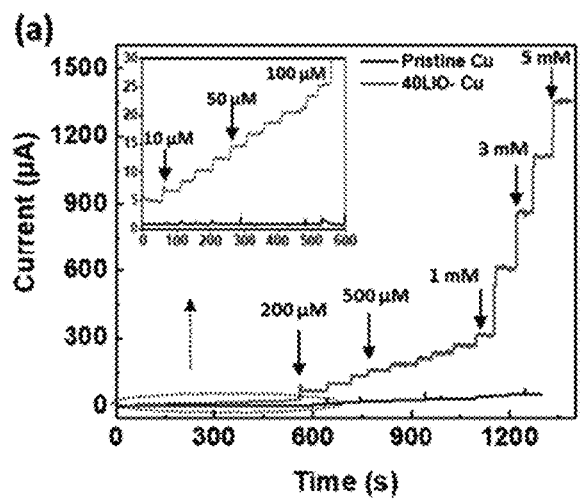
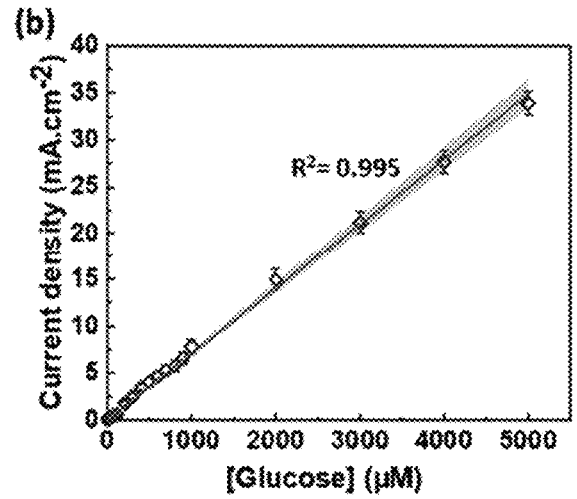
FIG. 10A  FIG. 10B
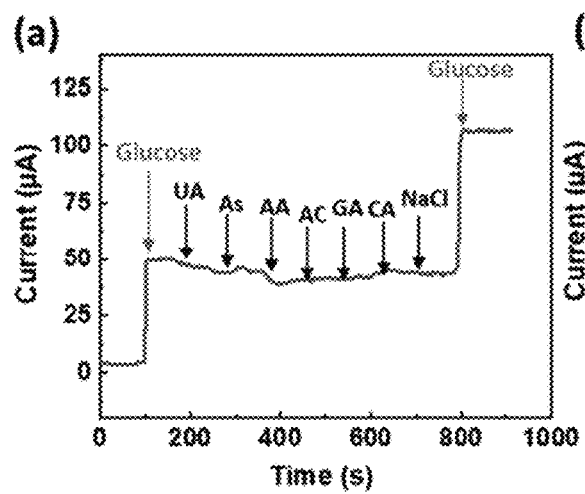
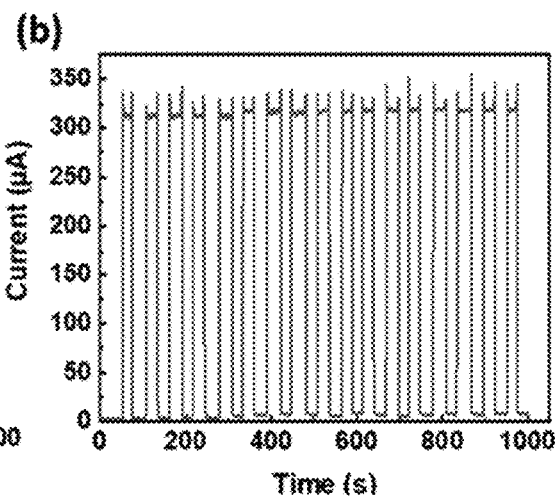
FIG. 11A  FIG. 11B

LASER-INDUCED ATMOSPHERIC $Cu_xO$ FORMATION ON COPPER SURFACE WITH ENHANCED ELECTROCHEMICAL PERFORMANCE

CROSS REFERENCE TO RELATED APPLICATIONS

This application claims the benefit of U.S. Provisional Application Ser. No. 63/235,590, filed on Aug. 20, 2021. The entire disclosure of the above application is hereby incorporated herein by reference.

FIELD

The present disclosure relates to laser processing approaches and, more particularly, to copper oxide ($Cu_xO$) structure formation through laser processing approaches.

INTRODUCTION

This section provides background information related to the present disclosure which is not necessarily prior art.

In the field of copper oxide ($Cu_xO$) structure formation, it is known that the copper oxide compounds chemical composition, distinct crystallographic feature and shape are key important factors that determine the overall physical and chemical properties of $Cu_xO$ structures. Cupric oxide (CuO) and cuprous oxide ($Cu_2O$) being the most common forms of the copper oxides with unique optical and electrical properties.

$Cu_xO$ structures have been used for a wide range of applications including electrochemical sensing, gas detection, photovoltaic energy conversion, bifouling prevention, and photochemical catalysis.

It is well known in the field that although $Cu_xO$ high-index facets structures containing a high density of low-coordinated atoms (including edges, steps, and kinks) offer highly active sites for catalysis and sensing applications, these facets are highly unstable and challenging to be prepared by traditional chemical synthesis and deposition techniques.

The primary approach to enhance catalytic activity of $Cu_xO$ structures with stable performance is to increase their effective surface area by synthesizing them in the form of micro/nano structures in low-index crystalline (i.e. the (111), (110), and (100) facets) or amorphous phases. Over the past decades, various routes for the synthesis of such unique $Cu_xO$ nanostructures have been investigated for different applications. However, many of such methods often involve use of complex processes not utilizing environmentally friendly chemicals and with long processing time.

The potential and simplicity of applying laser-induced oxidation (LIO) onto Cu metal surfaces to create unique $Cu_xO$ has been recognized in the art. Although limited studies have been published in the field, with LIO technologies application being related to enhancing optical properties, antibacterial performance, and corrosion resistance of Cu surfaces. For instance, the LIO technology applied Cu metal surfaces with controlled laser beams have been associated with the formation of robust porous metal oxide nanostructures of $Cu_2O$ and CuO by Boinovich et al.

There is a long need for studies of the effect of laser processing conditions, such as laser power, on the obtained $Cu_xO$ composition, micro/nano structure, and electrochemical sensing, and the correlation between those generated structures with electrochemical performance. The lack of publications in the field obviates the long need of the potential, but not yet demonstrated technique of direct LIO onto Cu surface for $Cu_xO$ nanostructure formation with enhanced electrochemical performance for application in biosensing.

Accordingly, there is a continuing need for $Cu_xO$ nanostructures properly immobilized onto a conductive electrode surface as a functional coating for catalytic and biosensing application. Hence, it would be advantageous to have a method for scalable synthesis of functional $Cu_xO$ nanostructures onto a copper surface utilizing environmentally friendly chemicals and conditions, with short processing time.

SUMMARY

In concordance with the instant disclosure, a method for scalable synthesis of functional copper oxide ($Cu_xO$) nanostructures onto a copper (Cu) surface utilizing environmentally friendly chemicals and conditions, with short processing time, has been surprisingly discovered.

In one aspect, this disclosure is related to a method of manufacturing and use of a $Cu_xO$ coating layer onto a Cu surface. In some exemplary embodiments, the method may include a fast one-step and reagent-less fabrication of electroactive hierarchical $Cu_xO$ with micro/nano structure directly onto a Cu surface by laser-induced oxidation (LIO) in ambient conditions, wherein the generated heat from the laser beam provides enough energy for the oxidation of Cu surface in the presence of atmospheric oxygen.

Further, the one-step fabrication may comprise of a superficial oxidation process, wherein the laser beam provides enough energy to oxidize Cu to form cuprous oxide ($Cu_2O$) and to further oxidize the $Cu_2O$ species to form cupric oxide (CuO).

Still further, fine particles created through a fast melting and fusion at high laser powers during the superficial oxidation process may accelerate the oxidation process itself. In another aspect, this disclosure is related to a $Cu_xO$ film with enhanced electrochemical performance for application in biosensing. In some exemplary embodiments, the film composition comprises of a well-defined copper oxide layer produced at the copper surface.

Further, the film composition comprises of $Cu_2O$ and CuO phases. In some embodiments, the $Cu_2O$ phase comprises a crystalline structure and the CuO phase is amorphous.

Still further, controlled LIO process leads to a controllable growth of $Cu_xO$ layer on the copper surface, wherein both $Cu_2O$ and CuO phases increase in quantity when increasing the laser power.

The present disclosure now will be described more fully hereinafter with reference to the accompanying drawings, which are intended to be read in conjunction with both this summary, the detailed description and any preferred and/or particular embodiments specifically discussed or otherwise disclosed. This present disclosure may, however, be embodied in many different forms and should not be construed as limited to the embodiments set forth herein; rather, these embodiments are provided by way of illustration only and so that this disclosure will be thorough, complete and will fully convey the full scope of the present disclosure to those skilled in the art. Further areas of applicability will become apparent from the description provided herein.

It should be understood that the description and specific examples are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

FIG. 3F is the plotted particle size distribution;

FIG. 4A is the nitrogen adsorption-desorption isotherm curves of pristine and 40LIO-Cu samples;

FIG. 4B is the Barret-Joyner-Halena (BJN) plots showing pore-size distribution;

FIG. 6C is the change in (111) crystalline phase by changing laser power;

FIG. 7A is the Raman spectra of pristine copper and LIO-Cu surfaces fabricated by different laser powers;

FIG. 7B is the change in the ratio of CuO to $Cu_2O$ Raman peak intensities by laser power;

FIG. 8A is the effect of laser power on electrochemical behavior of LIO-Cu samples, shown by CV curves in 0.1 M NaOH (−0.8, +0.8 V); Scan rate: 50 mV s−1 for different LIO-Cu samples;

FIG. 8B is the effect of laser power on electrochemical behavior of LIO-Cu samples, shown by change in main CV oxidation and reduction current density at about −0.6, −0.1, and +0.6 V, by laser power applied for fabrication of LIO-Cu electrodes;

FIG. 9A is the CV curve for different LIO-Cu samples in 1 mM glucose solution, scan rate: 50 mV s−1;

FIG. 9B is the CV curve for pristine-Cu in different glucose concentrations, scan rate: 50 mV s−1;

FIG. 9C is the CV curve for 40LIO-Cu in different glucose concentrations, scan rate: 50 mV s−1;

FIG. 9D is the comparison of current change versus glucose concentration at about +0.6 V for pristine Cu and 40LIO-Cu electrodes;

FIG. 10A is the chronoamperometric response of LIO-Cu towards glucose, shown by the amperometric stepwise response of pristine copper and 40LIO-Cu electrodes for successive addition of glucose to PBS buffer solution by applying +0.6 V potential;

FIG. 10B is the chronoamperometric response of LIO-Cu towards glucose, shown by the change in current with glucose concentration;

FIG. 11A is the glucose detection performance of LIO-Cu electrode, shown by selective response of the 40LIO-Cu electrode towards glucose in the presence of different interfering agents;

FIG. 11B is the glucose detection performance of LIO-Cu electrode, shown by response reproducibility of 40LIO-Cu electrode towards single concentration of glucose, 250 μM;

DETAILED DESCRIPTION

Figures 1A, 1B:
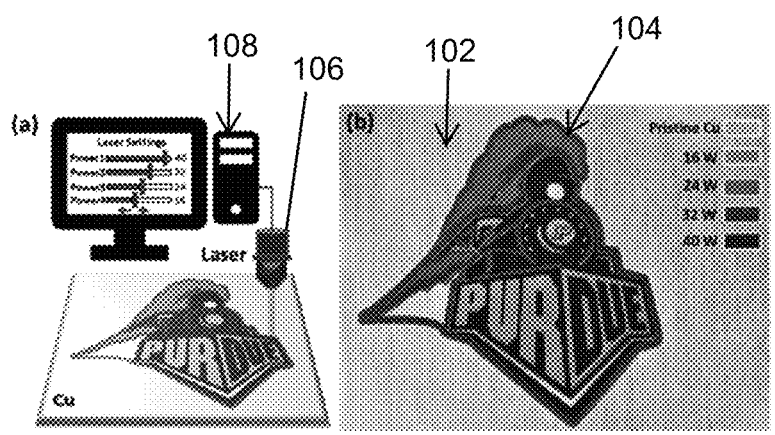
FIG. 1A is an illustration schematic of a process for drawing of a computer-controlled pattern onto the copper surface;140
FIG. 1B is an illustration of a copper surface irradiated by a ND:YAG laser beam under ambient condition. As it is depicted in FIG. 1B, irradiation of the Cu surface converted the surface to a dark copper oxide film.

The following description of technology is merely exemplary in nature of the subject matter, manufacture, and use of one or more present disclosures, and is not intended to limit the scope, application, or uses of any specific present disclosure claimed in this application or in such other applications as may be filed claiming priority to this application, or patents issuing therefrom. Regarding methods disclosed, the order of the steps presented is exemplary in nature unless otherwise disclosed, and thus, the order of the steps can be different in various embodiments, including where certain steps can be simultaneously performed.

I. Definitions

Unless otherwise defined, all technical terms used herein have the same meaning as commonly understood by one of ordinary skill in the art to which the present disclosure pertains.

As used herein, the terms "a" and "an" indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters. In the present disclosure the terms "about" and "around" may allow for a degree of variability in a value or range, for example, within 10%, within 5%, or within 1% of a stated value or of a stated limit of a range. Likewise, in the present disclosure the term "substantially" can allow for a degree of variability in a value or range, for example, within 90%, within 95%, or within 99% of a stated value or of a stated limit of a range.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components, or processes (for consisting of) and excluding additional materials, components or processes affecting the significant properties of the embodiment (for consisting essentially of), even though such additional materials, components or processes are not explicitly recited in this application. For example, recitation of a process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below," or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present disclosure includes a method of manufacturing a copper oxide ($Cu_xO$) structure onto a Copper (Cu) surface. The method may include providing the Cu surface and a laser source. The laser source may be a ND:YAG laser beam. Next, the method may include fabricating an electroactive hierarchical $Cu_xO$ structure directly onto the Cu surface by laser-induced oxidation (LIO), wherein the generated heat from the laser source provides energy for the oxidation of the Cu surface in the presence of atmospheric oxygen. The energy provided from the laser may oxidize the Cu to form cuprous oxide ($Cu_2O$). The $Cu_2O$ may then be oxidized to form cupric oxide (CuO). In a specific example, the electroactive hierarchical $Cu_xO$ structure may a micro-sized structure and/or a nano-sized structure. In another specific example, the step of fabricating the electroactive hierarchical $Cu_xO$ structure directly onto the Cu surface may particularly be a reagent-less form of fabrication.

In certain circumstances, a plurality of electroactive hierarchical CuxO structures may be fabricated onto the Cu surface, thus forming a $Cu_xO$ film. The film composition may include a CuO layer disposed on the copper surface. In a specific example, the film composition may include $Cu_2O$ and/or CuO phases. In a more specific example, the $Cu_2O$ phase may comprise a crystalline structure and the CuO phase may be amorphous.

In certain circumstance, the method may further include a step of providing a computer having a processor and a memory. The memory may include processor readable instructions for enabling computer-controlled laser scribing of the electroactive hierarchical $Cu_xO$ structure. The method may further include a step of autonomously laser scribing the electroactive hierarchical $Cu_xO$ structure in a predetermined design onto the Cu surface. In a specific example, the method may further include a step of adjusting a variable power output of the laser source during the step of autonomously laser scribing the electroactive hierarchical $Cu_xO$ structure in a predetermined design onto the Cu surface. In a more specific example, the variable power output of the laser source may be between around sixteen watts and around forty watts. In another specific example, the method may include a step of utilizing the fabricated electroactive hierarchical $Cu_xO$ structure on the Cu surface as a glucose sensor. In certain circumstances, the fabricated electroactive hierarchical $Cu_xO$ structure on the Cu surface used as a glucose sensor may more specifically be a binder-free nano-textured structure.

In certain circumstances, the present disclosure may also include a copper-based sensor configured to detect non-enzymatic glucose. The copper-based sensor may include a copper (Cu) surface and an electroactive hierarchical $Cu_xO$ structure coupled to the Cu surface via laser induced oxidation. Advantageously, the electroactive hierarchical $Cu_xO$ structure may have a stability of around 90 percent of the initial sensitivity after fifty days. In a specific example, the electroactive hierarchical $Cu_xO$ structure may more specifically be a binder-free nanostructure.

As shown in FIG. 1A, a computer-controlled process for drawing patterns onto the copper surface was utilized. As depicted in FIG. 1B, irradiation of the Cu surface by a ND:YAG laser beam under ambient conditions converted the Cu surface to a dark copper oxide ($Cu_xO$) film. By employing a computer-controlled laser scribing, LIO pattern can be readily written into the desired geometry as shown in FIG. 1B. The figure illustrated a patterned train logo on the Cu surface with five distinguished colors, each of which is attributed to an oxidation degree of Cu displaying the effect of laser induction with specific powers of an exemplary embodiment of the present disclosure.

Figure 2A:
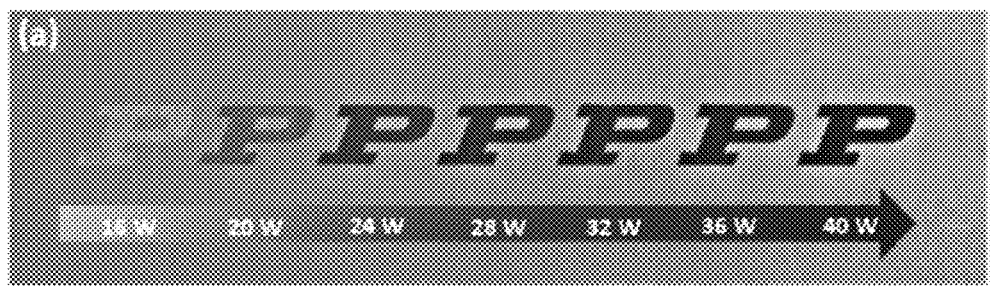
FIG. 2A is a realistic picture of an LIO copper surface that is patterned with a logo applying laser powers ranging from 16 W to 40 W with a constant irradiation time.
Figures 2B, 2C, 2D, 2E:
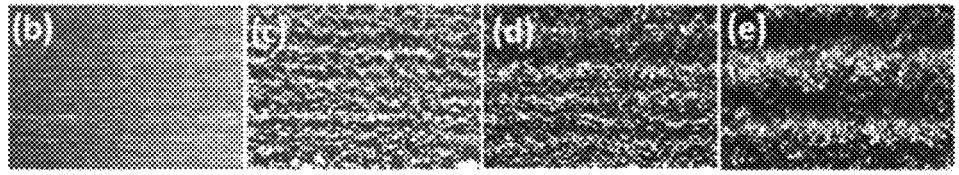
FIG. 2B is an optical microscopic image of an untreated pristine copper surface.
FIG. 2C is an optical microscopic image of LIO-Cu surface fabricated using 16 W laser power.
FIG. 2D is an optical microscopic image of LIO-Cu surface fabricated using 20 W laser power.
FIG. 2E is an optical microscopic image of LIO-Cu surface fabricated using 24 W laser power.
Figures 2F, 2G, 2H, 2I:
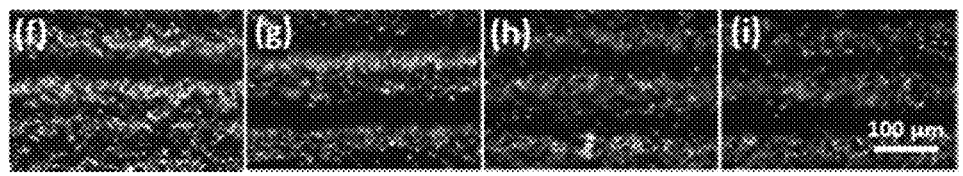
FIG. 2F is an optical microscopic image of LIO-Cu surface fabricated using 28 W laser power.
FIG. 2G is an optical microscopic image of LIO-Cu surface fabricated using 32 W laser power.
FIG. 2H is an optical microscopic image of LIO-Cu surface fabricated using 36 W laser power.
FIG. 2I is an optical microscopic image of LIO-Cu surface fabricated using 40 W laser power.
Figures 3A, 3B, 3C, 3D, 3E:
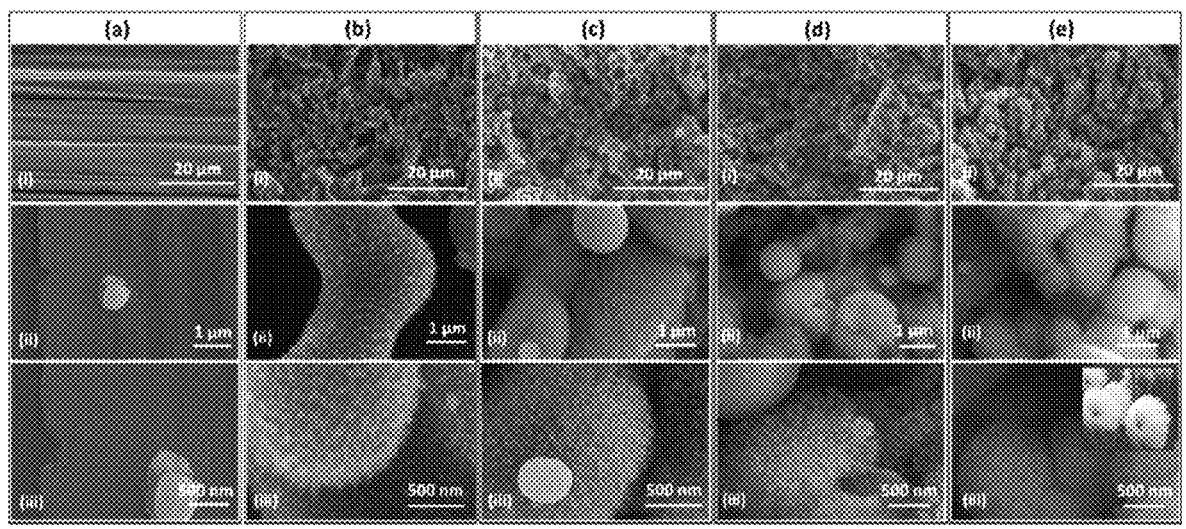
FIG. 3A is an SEM micrograph of pristine copper an untreated pristine copper surface, with (i) low, (ii) medium, and (iii) high magnifications.
FIG. 3B is an SEM micrograph of LIO-Cu surface fabricated using 16 W laser power, with (i) low, (ii) medium, and (iii) high magnifications.
FIG. 3C is an SEM micrograph of LIO-Cu surface fabricated using 24 W laser power, with (i) low, (ii) medium, and (iii) high magnifications.
FIG. 3D is an SEM micrograph of LIO-Cu surface fabricated using 32 W laser power, with (i) low, (ii) medium, and (iii) high magnifications.
FIG. 3E is an SEM micrograph of LIO-Cu surface fabricated using 40 W laser power, with (i) low, (ii) medium, and (iii) high magnifications.

FIG. 2A illustrates the assessment of the power effect on the morphology and microstructure of the Cu surface, by microscopic imaging and surface profilometry of copper samples processed at different laser power settings. FIG. 2A displays a realistic picture of an LIO copper surface that is patterned with a logo applying laser powers ranging from about 16 W to about 40 W with a constant irradiation time. It was observed that at about 16 W, copper color changed to a dominated red that was attributed to the oxidation of copper to $Cu_2O$. Increasing the laser power (samples >24 W) provided enough energy for the further oxidation of $Cu_2O$ to CuO. CuO renders the dark red (brown-ish) color. Increasing laser power to 40 W led to a darker surface, which can be explained by the increase in the ratio of CuO species. As further illustrated in FIGS. 2B-I the gradual darkening of the surface as a result of increased oxidation degree by optical microscopic imaging of the Cu surfaces. These images also illustrate a developed roughness on the surface of the LIO-Cu samples because of the laser texturing phenomena.

In some exemplary embodiments, ND:YAG laser with a common Gaussian beam profile is used. Other exemplary embodiments, utilizes LIO-Cu samples that can be formed by laser scribing with a spot diameter of about 40 μm, producing stripped patterns onto the surface. These LIO-Cu microtextured rough structures can provide high surface area for a variety of catalytic and electrocatalytic applications.

FIGS. 3A-E illustrate microstructure morphology and feature size of untreated Cu surface and the LIO-Cu structures by scanning electron microscope (SEM) imaging of the surfaces. SEM images of the untreated pristine Cu and four LIO-Cu samples prepared with different laser powers of about 16, 24, 32, and 40 W are shown respectively in FIGS. 3A-E (i), (ii), and (iii). As observed, the pristine Cu had a uniform surface with a dense metallic structure. The high magnification images of the pristine Cu also showed smooth surface with some intrinsic structural defects and lamellar morphology. Low-magnification SEM images clearly showed a highly textured microstructure generated by laser beam on all LIO-Cu surfaces. While the 16LIO-Cu surface represents a randomly oriented microstructure, raising the laser processing power to 24 W and 32 W let to the formation of more uniform microsphere structures of smaller sizes. By elevating the laser power to about 40 W, a larger quantity of small spherical particles was formed. The average diameter of generated spheres on 40LIO-Cu sample was about 1.23±0.33 μm.

In some exemplary embodiments, the laser beam with optimized powers can induce growth of well-oriented copper oxide microspheres on copper surface with small size distribution. Laser power can not only change the microstructure of the LIO samples but may also affected the final nanostructure on the textured microspheres which resulted in a unique hierarchical micro/nano scale combined copper oxide structure. In the 16LIO-Cu sample, some fine nanofeatures were visible at the surface of the microstructure which increased in quantity and ablation depth by raising the laser power to about 24 W and 32 W, respectively. The high magnification images of the 40LIO-Cu sample illustrate a highly oriented cotton-grass like structure with nanowhiskers that covered the surface. The insect in FIG. 3E(iii) represents a realistic image of a cotton-grass plant provided for structure comparison.

In some embodiments, the interaction of a high-power laser beam with copper surface, accompanied by deep engraving of the surface via local heating, can be followed by a rapid cooling of the surface. This localized laser-induced sublimation of the copper surface can result in formation of copper oxide nanoparticles that are subsequently self-organized and led to a hierarchical growth of the LIO-Cu structures on the surface as evidenced in the SEM images. At high laser power (e.g., ~40 W), laser beam provided high heat with greater ablation depth. The high temperature change between the heating step and subsequent rapid cooling of the surface caused an intense accumulation of the surface stress and grain refinement that resulted in formation of finer microparticles. The ablation profile and surface morphology can be considered as a function of the spatial intensity distribution of the incident laser beam.

FIG. 4A provides a graphical illustration of the Brunauer-Emmett-Teller (BET) isotherm for N2 adsorption-desorption analysis of the surface area and porosity for the 40LIO-Cu surface. As shown in FIG. 4B, a type IV isotherm (based on IUPAC reports) with a H3 type hysteresis representing presence of mesoporous structure was obtained and confirmed by the Barrett-Joyner-Halenda (BJH) pore size distribution. The BJH data shows the pore sizes distributed between 4-10 nm, representing mesoporous structure (typically 2-50 nm). BET analysis of 40LIO-Cu samples showed that the majority of the pores were within the range 5 nm with high effective surface area of 0.125 m2 g−1.

Figure 5A:
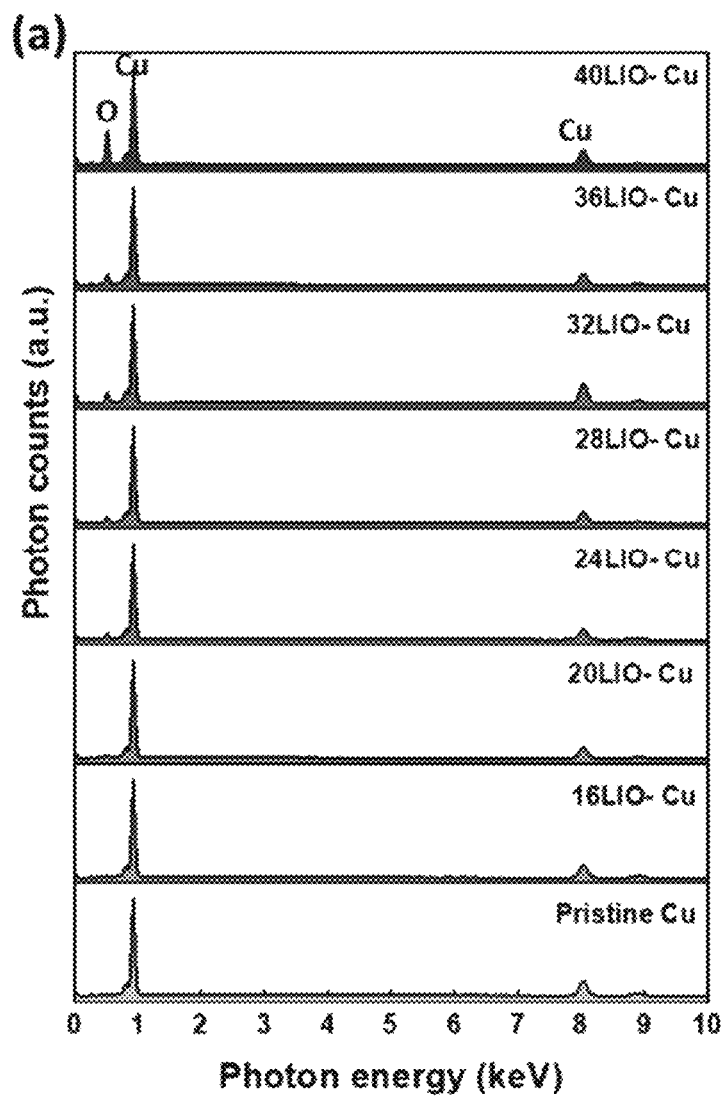
FIG. 5A is the EDX plots for pristine Cu and LIO-Cu samples.
Figure 5B:
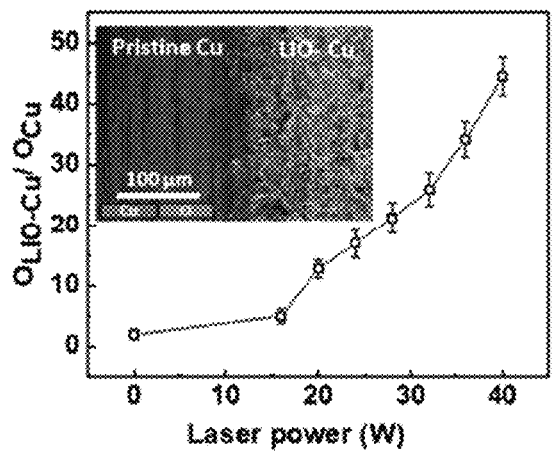
FIG. 5B is the relative change in the level of oxygen by laser power curve; inset is EDX copper-oxygen map of 40LIO-Cu sample.
Figure 5C:
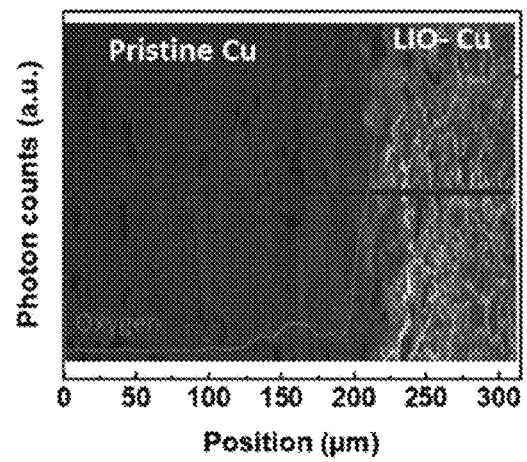
FIG. 5C is the EDX line-scan for oxygen change on the 40LIO-Cu surface with associated sample in the background.

FIG. 5A provides a graphical illustration of the EDX analysis for pristine and different LIO-Cu samples, which clearly revealed the increase in the oxygen level in the composition of these surfaces when increasing the laser power. FIG. 5B displays the ratio of oxygen in LIO-Cu samples compared to the oxygen in the pristine sample with respect to the change in laser power. As the laser power is elevated, the oxygen ratio increased and finally at 40 W, the oxygen ratio enhanced significantly as compared to the pristine copper, representing high level of copper oxidation. The high level of oxidation is confirmed by the inset image in the FIG. 5B in EDX oxygen mapping of a sample depicting both pristine and LIO-Cu areas. The two-sides surface was further analyzed for EDX line-scan which is shown in FIG. 5C. FIG. 5C demonstrates the enhanced oxygen level that is initiated from the boundary of the pristine copper and LIO-Cu area which has been affected by the generated heat at the joint LIO section.

Figure 6A:
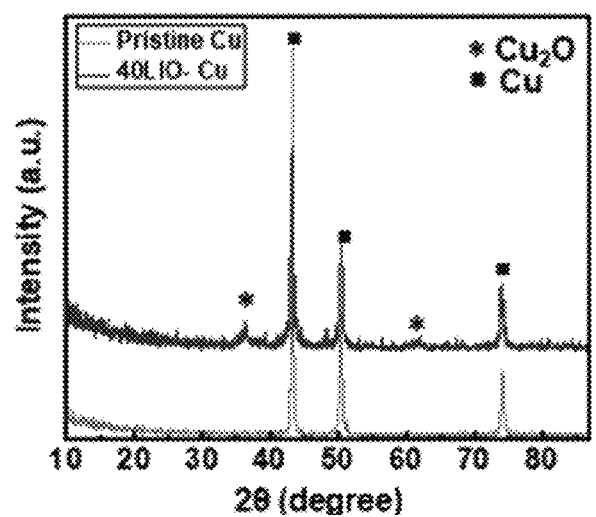
FIG. 6A is the GI-XRD spectra for pristine and 40L10 Cu sample.
Figure 6B:
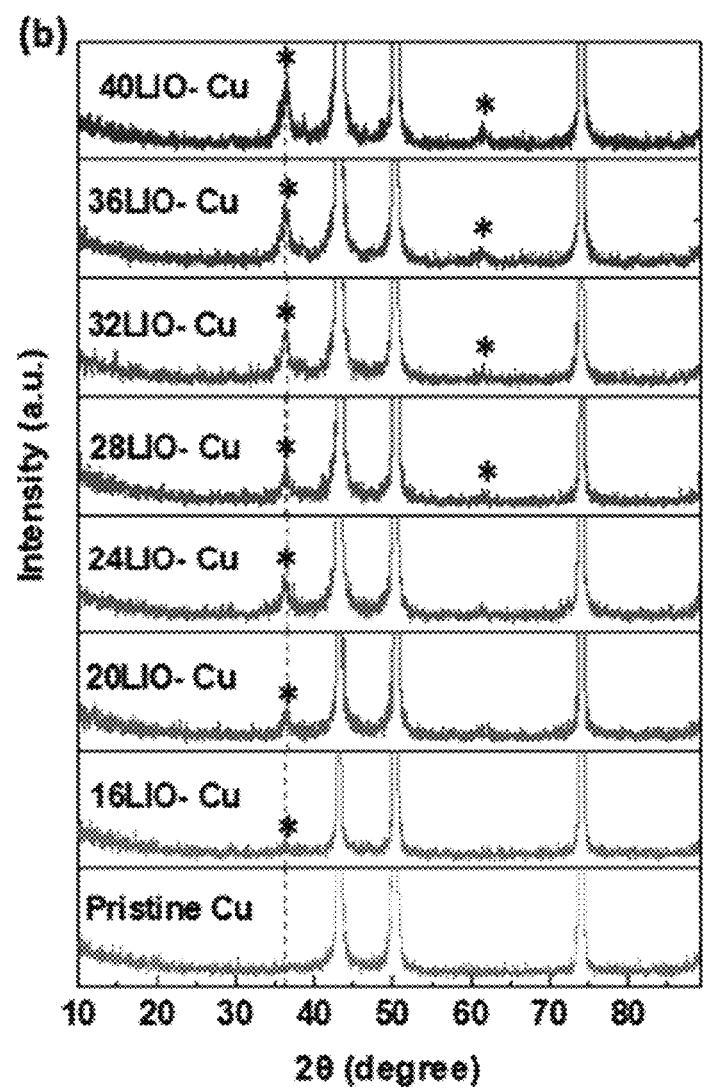
FIG. 6B is the comparison of XRD spectra of pristine and different LIO-Cu samples tuned by laser power.

FIGS. 6A-C provide a graphical illustration of the crystalline structures of the pristine copper and the LIO-Cu surfaces analyzed by GI-XRD. XRD patterns for pristine copper and LIO-Cu samples in FIG. 6A exhibit intense peaks at 2θ values of 43.3°, 50.3°, and 73.4°, which are respectively indexed to the reflections from (111), (200), and (220) Cu planes with face-centered-cubic crystallinity (JCPDS 04-0836, and 01-085-1326). In addition, the LIO-Cu samples showed a diffraction peak appeared at about 2θ=36.47°, which can be attributed to the single-phase $Cu_2O$ (111) plane with a monoclinic structure (JCPDS 34-1354 and 01-078-2076). This low-index crystalline facet made by a prompt LIO process, possesses excellent electrochemical and optical properties, and can provide suitable sites for various catalytic, optical, and sensing applications.

FIG. 6B provides a graphical illustration of comparative XRD patterns depicting the effect of laser power on the crystalline structure of the LIO-Cu film. FIG. 6C provides a graphical illustration of the changes in the intensity of $Cu_2O$ (111) peak versus laser power. Increasing the laser power from about 16 W to 40 W can provide a visible enhancement in the intensity of the $Cu_2O$ (111) peak. It is understood by these observations that besides increasing laser power, the increase in $Cu_2O$ may also be intensified due to the decrease of feature sizes (as shown in SEM images), which provided higher surface area to participate in the LIO oxidation reaction process. A new $Cu_2O$ peak also appeared at high laser power at 2θ=61.4°, which can be assigned to the (311) plane (JCPDS 01-078-2076).

FIG. 7A provides a graphical illustration of the Raman spectra, comparatively plotted, for the pristine copper and the LIO-Cu samples. A distinctive enhancement in the Raman shifts by laser power were attributed to the change in the copper oxide level. The Raman shift at about 638-665 cm-1 corresponded to the out-of-phase motion of Cu and O in $Cu_2O$ sublattice, which is known as T1U symmetry mode. Increase in this vibration mode confirmed the increase in the $Cu_2O$ sublattices, which was also evidenced by a crystalline structure shown in XRD analysis. Widening of this Raman shift by increasing the laser power can be explained by the decrease in the particle sizes which enhanced the Raman scattering. On the other hand, an intense Raman shift at between about 296-300 cm-1 was attributed to the Raman active vibration of Ag symmetry in the CuO structure. At high temperatures generated by the laser beam, the $Cu_2O$ were prone to be further oxidized to form CuO. In conventional procedures, this oxidation process can be limited by the diffusion through the thick oxide layer. In this disclosure, it was demonstrated that the superficial oxidation process and fine structure of the top oxide layer provided an opportunity for further oxidation of $Cu_2O$ into CuO. Interestingly, CuO phase produced in this process did not exhibit any crystalline phase as evidenced in the XRD spectra, implying the possibility for the formation of an amorphous structure caused by a prompt oxidation of $Cu_2O$ on the outer copper surface.

FIG. 7B compares the changes in the ratio of CuO to $Cu_2O$ Raman peak intensities. While the total oxide level can be increased by elevating the laser power, the CuO:$Cu_2O$ ratio appeared to increase. The peak corresponding to the CuO species exhibited a higher enhancement compared to that of $Cu_2O$. In the initial stages of the oxidation process, the formation of $Cu_2O$ took place as a result of the oxidation of copper. As the $Cu_2O$ layer was formed by the LIO process, the particles on the upper part of the surface were subjected to further oxidation leading to the concomitant formation of CuO on the LIO-Cu film. Absence of crystalline CuO peaks in the XRD spectra can be explained by a preferable formation of amorphous CuO phase on the copper surface though a prompt oxidation and re-organization process at the high laser power. However, amorphous phase of CuO is also reported to have high surface area exhibiting excellent electrochemical performance.

Electrochemical Study:

FIG. 8A provides graphical illustration of the cyclic voltammetry data, demonstrating the oxidation and reduction peaks on a small 2×2 mm2 area of the pristine and LIO-Cu samples in NaOH solution. This disclosure demonstrated the presence of high levels of electrochemically active species on the surface of LIO samples, as the total current values in the applied potential range (−0.8 to +0.8 V) were significantly higher for the LIO samples as compared to the pristine Cu. Anodic peaks at the applied potential values close to about −0.4, −0.1, and +0.6 V were attributed to the oxidation of Cu, $Cu_2O$ and CuO species, respectively. While the oxidation peaks of Cu(I) and Cu(II) were significantly enhanced. Increased anodic peak intensities by increasing the laser powers verified electrochemically active behavior of the low-index $Cu_2O$ (III) and amorphous CuO produced by the LIO technique disclosed herein.

FIG. 8B compares changes in the cathodic and anodic current versus laser power for one reduction and two oxidation potentials, respectively. The consistent gradual enhancement by increasing the laser power showed the capability of this process for controllable fabrication of electrochemically active species.

This disclosure has demonstrated that these electrochemically active species were promising structures for non-enzymatic glucose oxidation. The CV analysis in the presence of 1 mM glucose solution demonstrated the glucose oxidation at about +0.6 V in FIG. 9A. The highest oxidation peaks belonged to the 40LIO-Cu sample which possessed the highest CuO:$Cu_2O$ ratio, based on the characterization data. Electrocatalytic oxidation of the glucose on copper-oxide-based electrodes in an aqueous media was carried out through oxidation of the aldehyde functional group to a carboxylic acid group (equations (1), (2), and (3) below).

$$CuO + OH^- \rightarrow CuOOH + e^- \quad (1)$$

$$Cu(III) + glucose \rightarrow Gluconolactone + Cu(II) \quad (2)$$

$$Gluconolactone \rightarrow Gluconic\ acid \quad (3)$$

FIGS. 9B-C provide the CVs of pristine and 40LIO-Cu electrodes in different glucose concentrations ranging from 0 to 1 mM, respectively. The current change by increasing the glucose content was remarkably higher for 40LIO-Cu than that of the pristine Cu. The linear current change by glucose concentration is comparatively plotted in FIG. 9D, which indicates a notable difference in the slope for the 40LIO and pristine Cu electrodes. This is best understood and being due to the high quantity of electroactive components ($Cu_2O$ and CuO) and sufficient surface area for electrocatalytic reaction created by the laser texturing.

It should be noted that higher laser power not only resulted in higher copper oxide compounds and greater glucose sensitivity performance, but also resulted in deeper ablation depths into the metal substrate.

FIG. 10A shows a chronoamperometry plot for pristine Cu and 40LIO-Cu. While the produced current on pristine Cu by successive addition of glucose to the PBS solution was too low, 40LIO-Cu electrode showed an obvious current change even for the glucose concentrations as low as 10 μm. This electrode showed an exceptional sensitivity for a wide range of glucose concentrations from between about 10 μm to 5 mM with no further treatment or washing steps between the tests. This performance along with the fast response of the 40LIO-Cu electrodes were originated from its high surface area and electrocatalytic activity caused by the LIO technique disclosed herein.

FIG. 10B provides a graphical illustration of the current response of 40LIO-Cu electrode versus glucose concentration, which shows a linear behavior with an R2=0.995, suggesting this electrode as a reliable glucose sensor for a wide range of concentrations. The calculated slope was 0.00695±0.0001 mA μM−1 cm-2 (which was equal to the sensitivity of 6950 mA μM−1 cm-2) for a 2×2 mm2 electrode. The limit of detection (LOD) value was calculated as 2.81 μM using the following equation based on a signal-to-noise ratio of 3:LOD=3 S/m). Where S is the standard deviation calculated from the blank signals (PBS electrolyte without added glucose) and m is the slope of obtained calibration plot (FIG. 10B).

FIG. 11A demonstrates that the 40LIO-Cu electrode has a negligible current change by addition of interfering agents, while its response to glucose remained stable in the presence of all interfering agents. In some exemplary embodiments, the interfering agents were selected from the group consisting of uric acid (UA), L-ascorbic acid (As), acetic acid (AA), acetaminophen (AC), glutamic acid (GA), citric acid (CA), and NaCl. Possible interference from the different agents was studied by addition of 100 μM of glucose to the background PBS followed by successive addition of 100 μM of each agent.

FIG. 11B provides graphical illustration of the response reproducibility of the 40LIO-Cu electrode, which was evaluated for 17 cycles of switching from pure PBS to a PBS with 250 μM glucose. This disclosure has demonstrated a fast recovery time (estimated to be <3 seconds) and an appropriate response reproducibility of the 40LIO-Cu sensor toward glucose detection, indicating that this sensor can be used for multiple cycles without cleaning after each measurement.

Figure 11C:
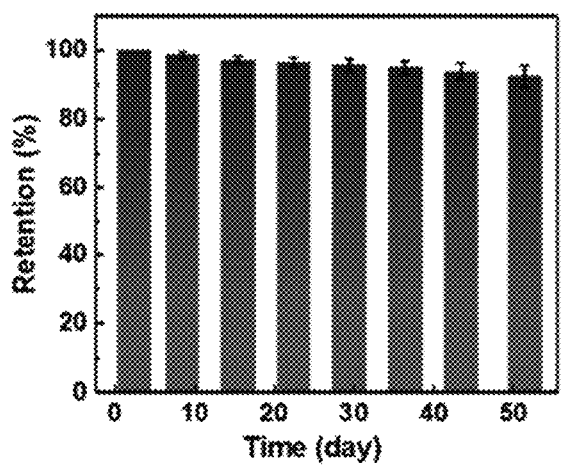
FIG. 11C is the glucose detection performance of LIO-Cu electrode, shown by long-term reusability of the 40LIO-Cu electrode for glucose detection in PBS buffer solution.

FIG. 11C provides graphical illustration of the long-term stability of the 40LIO-Cu sensor, shown by running amperometric test for a concentration range of 10 to 1000 μM glucose every week. As shown, this electrode showed high reusability in glucose sensing with a highly stable response. The recorded sensitivity after 50 days was about 92.3% of the initial sensitivity. It is understood that this is due its binder-free nanotextured structure which prevented the instability through leaching of the active sites.

Figure 11D:
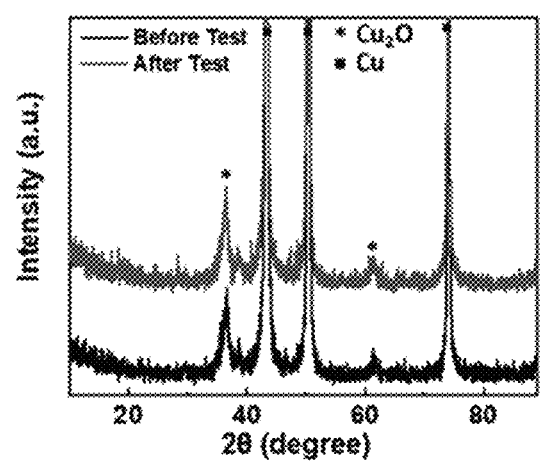
FIG. 11D is the glucose detection performance of LIO-Cu electrode, shown by comparison of XRD spectra for the LIO-Cu before and after glucose detection test in PBS (glucose concentrations of 5 mM)

FIG. 11D provides a graphical illustration of the comparison of GI-XRD spectra of the 40LIO-Cu electrode before and after glucose detection, which showed no significant change in the crystallographic structure on the LIO-Cu surface. This further confirms the stability of the copper oxide crystalline structure that was created on the copper surface by the LIO technique disclosed herein.

Figure 12:
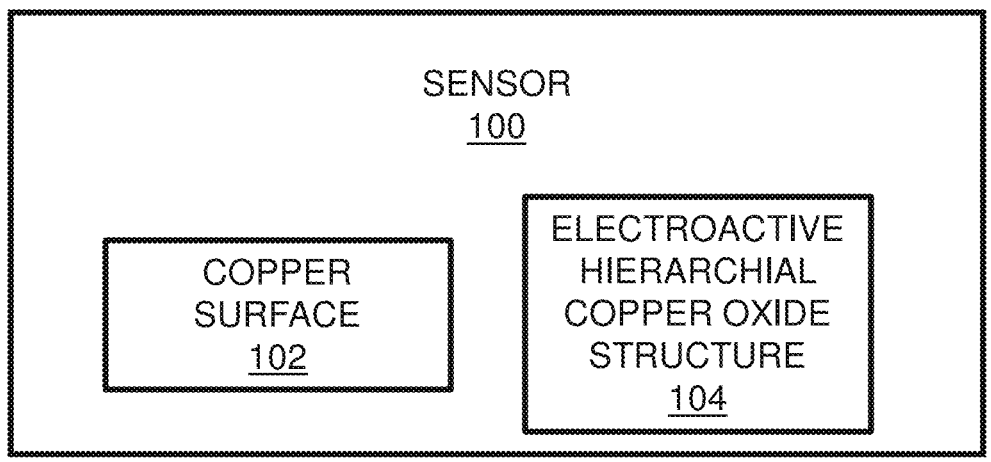
FIG. 12 is box diagram of a sensor, further depicting the sensor including a copper surface and an electroactive hierarchical copper oxide structure, according to one embodiment of the present disclosure.

FIG. 12 provides a block diagram illustrating a copper-based sensor 100 configured to detect non-enzymatic glucose. The copper-based sensor 100 may include a copper (Cu) surface 102 and an electroactive hierarchical $Cu_xO$ structure 104 coupled to the Cu surface 102 via laser induced oxidation.

Figure 13:
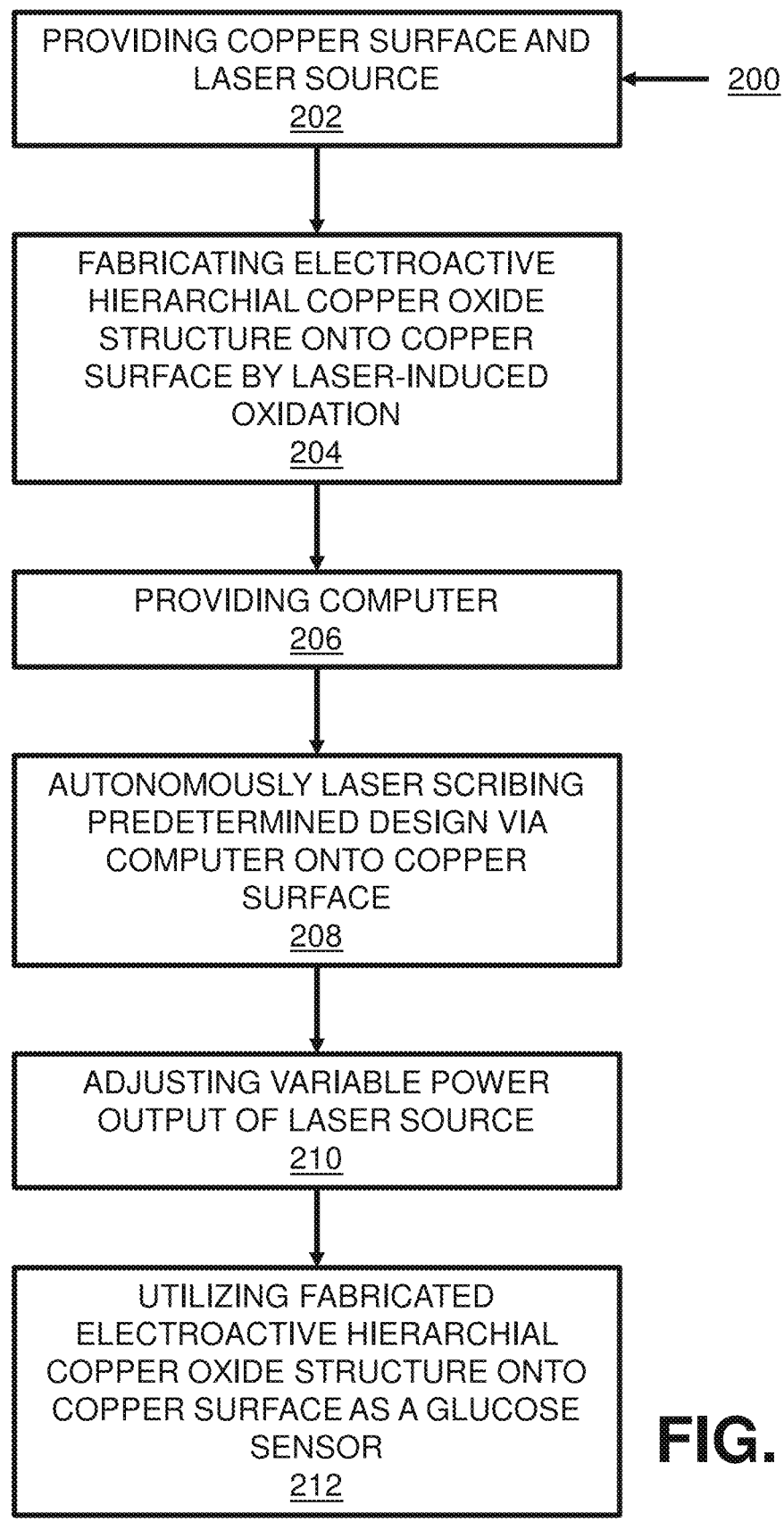
FIG. 13 is the flow diagram of a method for manufacturing a copper oxide structure onto a copper surface, according to one embodiment of the present disclosure.

FIG. 13 provides a flowchart illustrating a method 200 for manufacturing a copper oxide ($Cu_xO$) structure 104 onto a copper (Cu) surface 102. The method 200 may include providing the Cu surface 102 and a laser source 106. The laser source 106 may be a neodymium-doped yttrium aluminum garnet (ND:YAG) laser beam. Next, the method 200 may include fabricating the electroactive hierarchical CuxO structure 104 directly onto the Cu surface 102 by laser-induced oxidation (LIO), wherein the generated heat from the laser source 106 provides energy for the oxidation of the Cu surface 102 in the presence of atmospheric oxygen. The energy provided from the laser 106 may oxidize the Cu to form $Cu_2O$. The $Cu_2O$ may then be oxidized to form CuO. In a specific example, the electroactive hierarchical $Cu_xO$ structure 104 may a micro-sized structure and/or a nano-sized structure. The method 200 may further include a step 206 of providing a computer 108 having a processor and a memory, wherein the memory includes processor readable instructions for enabling computer-controlled laser scribing of the electroactive hierarchical $Cu_xO$ structure 104. Afterwards, the electroactive hierarchical $Cu_xO$ structure 104 may be autonomously laser scribed in a predetermined design onto the Cu surface. In a specific example, the method 200 may include a step 210 of adjusting a variable power output of the laser source 106 during the step of autonomously laser scribing the electroactive hierarchical $Cu_xO$ structure 104 in a predetermined design onto the Cu surface 102. In a more specific example, the fabricated electroactive hierarchical $Cu_xO$ structure 104 on the Cu surface 102 may then be utilized as a glucose sensor. It is contemplated that the fabricated electroactive hierarchical $Cu_xO$ structure 104 on the Cu surface 102 may be utilized for many biosensing applications. One skilled in the art may select other suitable methods of manufacturing the $Cu_xO$ structure onto the Cu surface, within the scope of the present disclosure.

Table 1, shown below, compares the performance of demonstrated LIO-Cu sensor in this disclosure with some previous reported copper-based non-enzymatic glucose sensors. The LIO-Cu of the present disclosure have shown excellent glucose detection performance, with significantly lower fabrication complexity. Specifically, LIO-Cu sensor outperformed most of the newly developed Cu-based sensors in sensitivity and long-term stability. This is best understood to be due to the LIO-Cu high surface area and binder-free nanostructure, which provided robust electrocatalytic sites for glucose oxidation process.

TABLE 1

Comparison of sensing behavior of the present disclosure with known Cu-based non-enzymatic glucose sensors. Measurements were performed using amperometric technique.

| Sensor Type | Preparation technique | Linear range (up to mM) | sensitivity ($\mu A\ mM^{-1}\ cm^{-2}$) | LOD ($\mu M$) | working potential (V) | long-term stability |
|---|---|---|---|---|---|---|
| LIO—CuO/Cu$_2$O | laser induced oxidation | 5 | 6950 | 2.81 | +0.6 | 50 days (92.3%) |
| NPG/CuO | electrodeposition | 12 | 374 | 2.8 | +0.4 | N/A |
| Cu$_x$O/polypyrrole/Au | electrodeposition | 8 | 232.22 | 6.2 | +0.6 | 10 days (96.2%) |
| CuO nanosheet/ carbon cloth | sputtering-wet etching | 1 | 4902 | 1 | +0.55 | 20 days (86.5%) |
| Cu(II)/MWCNT-COOH/GCE | sonication and drop-casting | 9 | 2149 | 0.3 | +0.6 | N/A |
| Nano-coral arrays Cu | electrodeposition | 5 | 1621 | 0.2 | +0.6 | 10 days (92.1%) |
| CuO NP/Pt | inkjet printing | 6 | 1600 | 0.5 | +0.5 | N/A |
| Cu NP-LIG | electroless deposition | 6 | 495 | 0.39 | +0.5 | 21 days (94.04%) |
| Cu$_x$O/Cu | laser enhanced thermal oxidation | 1.6 | 1212.06 | 10 | +0.4 | N/A |
| Cu-PAni composite | electrodeposition | 1 | 4140 | 5 | −0.45 | N/A |
| CuO hollow sphere | hydrothermal | 16 | 35.2 | 1 | +0.55 | N/A |
| CuS/Cu$_2$O/CuO/Cu nanowire array | Anodization-annealing | 4 | 4262 | 2 | +0.6 | 21 days (92%) |
| 3D Cu foam- CuONWA | wet-chemical method- annealing | 0.5 | 32330 | 0.02 | +0.55 | 12 days (94.1%) |

Advantageously, the Cu$_x$O structure on the Cu surface of the present disclosure may be manufactured with environmentally friendly chemicals, with a more efficient processing time. Desirably, the Cu$_x$O structure may provide enhanced sensitivity and long-term stability as a biosensor.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A method of manufacturing a copper oxide (Cu$_x$O) structure onto a Copper (Cu) surface, the method comprising the steps of:
   providing the Cu surface and a laser source; and
   fabricating an electroactive hierarchical Cu$_x$O structure directly onto the Cu surface by laser-induced oxidation (LIO), wherein the generated heat from the laser source provides energy for the oxidation of the Cu surface in the presence of atmospheric oxygen, and wherein the energy provided from the laser oxidizes the Cu to form Cu$_2$O.

2. The method of claim 1, wherein the electroactive hierarchical Cu$_x$O structure is a micro-sized structure.

3. The method of claim 1, wherein the electroactive hierarchical Cu$_x$O structure is a nano-sized structure.

4. The method of claim 1, wherein the step of fabricating the electroactive hierarchical Cu$_x$O structure directly onto the Cu surface is a reagent-less fabrication.

5. The method of claim 1, wherein the Cu$_2$O is oxidized to form CuO.

6. The method of claim 1, wherein a plurality of electroactive hierarchical Cu$_x$O structures are fabricated onto the Cu surface, thus forming a Cu$_x$O film.

7. The method of claim 6, wherein the film composition comprises of a CuO layer disposed on the copper surface.

8. The method of claim 7, wherein the film composition comprises at least one of Cu$_2$O and CuO phases.

9. The method of claim 8, wherein the Cu$_2$O phase comprises a crystalline structure and the CuO phase is amorphous.

10. The method of claim 1, wherein the laser source is a ND:YAG laser beam.

11. The method of claim 1, further comprising a step of providing a computer having a processor and a memory, wherein the memory includes processor readable instructions for enabling computer-controlled laser scribing of the electroactive hierarchical Cu$_x$O structure.

12. The method of claim 11, further comprising a step of autonomously laser scribing the electroactive hierarchical Cu$_x$O structure in a predetermined design onto the Cu surface.

13. The method of claim 12, further comprising a step of adjusting a variable power output of the laser source during the step of autonomously laser scribing the electroactive hierarchical Cu$_x$O structure in a predetermined design onto the Cu surface.

14. The method of claim 13, wherein the variable power output of the laser source is between around sixteen watts and around forty watts.

15. The method of claim 1, further comprising a step of utilizing the fabricated electroactive hierarchical Cu$_x$O structure on the Cu surface as a glucose sensor.

16. The method of claim 15, wherein the fabricated electroactive hierarchical $Cu_xO$ structure on the Cu surface used as a glucose sensor is a binder-free nanotextured structure.

17. A method of manufacturing a copper oxide ($Cu_xO$) structure onto a Copper (Cu) surface, the method comprising the steps of:

provides the Cu surface and a laser source;

fabricating an electroactive hierarchical $Cu_xO$ structure directly onto the Cu surface by laser-induced oxidation (LIO), wherein the generated heat from the laser source provides energy for the oxidation of the Cu surface in the presence of atmospheric oxygen; and providing a computer having a processor and a memory, wherein the memory includes processor readable instructions for enabling computer-controlled laser scribing of the electroactive hierarchical $Cu_xO$ structure.

* * * * *